United States Patent
Nissan et al.

(10) Patent No.: US 8,961,600 B2
(45) Date of Patent: Feb. 24, 2015

(54) METHOD OF USING A FIBER MATRIX FOR MAINTAINING SPACE IN SOFT TISSUES

(75) Inventors: Oded Nissan, Modiin (IL); Ira Yaron, Har Adar (IL); Jonathan Ben-Zvi, Qiriat-Tivon (IL)

(73) Assignee: Optonol Ltd., Neve Ilan (IL)

(*) Notice: Subject to any disclaimer, the term of this patent is extended or adjusted under 35 U.S.C. 154(b) by 799 days.

(21) Appl. No.: 12/823,640

(22) Filed: Jun. 25, 2010

(65) Prior Publication Data

US 2010/0331975 A1 Dec. 30, 2010

Related U.S. Application Data

(60) Provisional application No. 61/220,393, filed on Jun. 25, 2009.

(51) Int. Cl.
- *A61F 2/14* (2006.01)
- *A61F 9/007* (2006.01)
- *A61L 27/16* (2006.01)
- *A61L 27/18* (2006.01)

(Continued)

(52) U.S. Cl.
CPC ............ *A61F 9/00781* (2013.01); *A61L 27/16* (2013.01); *A61L 27/18* (2013.01); *A61L 31/048* (2013.01); *A61L 31/06* (2013.01); *A61L 2430/16* (2013.01); *A61L 2430/32* (2013.01); *A61L 2430/34* (2013.01); *Y10S 623/905* (2013.01)
USPC .............................. 623/4.1; 623/905; 128/898

(58) Field of Classification Search
CPC ............................................ A61F 2009/00865
USPC .......................... 623/4.1, 6.64, 905; 128/898
See application file for complete search history.

(56) References Cited

U.S. PATENT DOCUMENTS

| 4,060,081 A | 11/1977 | Yannas et al. |
| 4,634,418 A | 1/1987 | Binder |
| 5,433,701 A * | 7/1995 | Rubinstein ......................... 604/8 |

(Continued)

FOREIGN PATENT DOCUMENTS

| EP | 1 068 877 A1 | 1/2001 |
| WO | 2004/064694 A1 | 8/2004 |

(Continued)

OTHER PUBLICATIONS

Liu et al, "Ultrafine Fibrous Cellulose Membranes from Electrospinning of Cellulose Acetate", Fiber and Polymer Science, vol. 40, Issue 18, pp. 2119-2129, (Aug. 2002).*

(Continued)

*Primary Examiner* — Paul Prebilic
(74) *Attorney, Agent, or Firm* — Kenyon & Kenyon LLP

(57) ABSTRACT

A fiber matrix is provided for maintaining space in soft tissue, for example for use in procedures for assisting drainage of aqueous humor from an eye to treat glaucoma. The fiber matrix comprises a plurality of crossing fibers forming a mesh with a plurality of void spaces. The fibers and void spaces are sized and arranged so as to permit passage of fluid through the fiber matrix and to inhibit formation of scar tissue through the fiber matrix. The fibers may comprise a polymeric material, and the fiber matrix may be manufactured by electrospinning. The fibers may comprise a biostable and/or a biodegradable material. In one method of using a fiber matrix, the fiber matrix is positioned under a scleral flap, with at least part of the fiber matrix under the scleral flap.

45 Claims, 5 Drawing Sheets

(51) Int. Cl.
*A61L 31/04* (2006.01)
*A61L 31/06* (2006.01)

(56) References Cited

U.S. PATENT DOCUMENTS

| | | | |
|---|---|---|---|
| 5,489,304 A | | 2/1996 | Orgill et al. |
| 5,573,544 A | * | 11/1996 | Simon et al. .................. 606/151 |
| 5,681,275 A | * | 10/1997 | Ahmed .............................. 604/9 |
| 6,013,628 A | | 1/2000 | Skubitz et al. |
| 6,063,116 A | | 5/2000 | Kelleher |
| 6,102,045 A | | 8/2000 | Nordquist et al. |
| 6,218,360 B1 | | 4/2001 | Cintron et al. |
| 6,284,451 B1 | * | 9/2001 | Funatsu et al. .................. 435/1.1 |
| 6,299,895 B1 | | 10/2001 | Hammang et al. |
| 2002/0165478 A1 | * | 11/2002 | Gharib et al. ...................... 604/8 |
| 2004/0121943 A1 | | 6/2004 | Hsu et al. |
| 2005/0143817 A1 | * | 6/2005 | Hunter et al. ............... 623/11.11 |
| 2006/0235367 A1 | * | 10/2006 | Takashima et al. ........... 604/541 |
| 2010/0137981 A1 | * | 6/2010 | Silvestrini et al. ............. 623/4.1 |

FOREIGN PATENT DOCUMENTS

| | | |
|---|---|---|
| WO | 2007/060433 A1 | 5/2007 |
| WO | 2007/087061 A2 | 8/2007 |
| WO | 2008/112304 A1 | 9/2008 |
| WO | 2009/158524 A2 | 12/2009 |

OTHER PUBLICATIONS

Notification of Transmittal with International Search Report and the Written Opinion of the International Searching Authority, mailed Oct. 5, 2010, from related International Application No. PCT/US2010/040010.
Compton, Carolyn C., et al., "Organized Skin Structure Is Regenerated In Vivo from Collagen-GAG Matrices Seeded with Autologous Keratinocytes," The Journal of Investigative Dermatology, vol. 110, No. 6, pp. 908-916 (Jun. 1998).
Concordia Medical, "Concordia Medical's New BIOFELT™ Tissue Engineering Scaffolds Contribute to the Growing Field of Regenerative Medicine," Press Release, Coventry, Rhode Island (Feb. 13, 2008).
Dahan, Elie, MD, et al., "Comparison of the Efficacy and Longevity of Nonpenetrating Glaucoma Surgery With and Without a New, Nonabsorbable Hydrophilic Implant," Ophthalmic Surgery, Lasers & Imaging, vol. 34, No. 6, pp. 457-463 (Nov.-Dec. 2003).
Gore BIO—A Tissue Reinforcement, Instructions for Use, W.L. Gore & Associates, Inc. (Aug. 2008).
Gore BIO—A Tissue Reinforcement, product brochure, W.L. Gore & Associates, Inc. (Jun. 2008).
Jordan, David R., M.D., et al., "The Use of Vicryl Mesh in 200 Porous Orbital Implants—A Technique With Few Exposures," Ophthalmic Plastic & Reconstructive Surgery, vol. 19, No. 1, pp. 53-61 (Jan. 2003).
Muños, Gonzalo, MD, Ph.D., "Nonstitch Suprachoroidal Technique for T-flux Implantation in Deep Sclerectomy," J. Glaucoma, vol. 18, No. 3, pp. 262-264 (Mar. 2009).
Orgill, Dennis P., Ph.D., et al., "Behavior of Collagen—GAG Matrices as Dermal Replacement in Rodent and Porcine Models," Wounds: A Compendium of Clinical Research and Practice, vol. 8, No. 5, pp. 151-157 (Sep.-Oct. 1996).
"SkGel implant provides stable IOP," Ophthalmology Times Europe (Feb. 22, 2008).
"T.Flux glaucoma implant effectively reduces IOP," Glaucoma—Ocular Surgery News Europe/Asia-Pacific Edition (May 1, 2001).
Yannas, I.V., et al., "Wound Tissue Can Utilize a Polymeric Template to Synthesize a Functional Extension of Skin," Science, vol. 215, pp. 174-176 (Jan. 8, 1982).
Yannas, I.V., et al., "Synthesis and characterization of a model extracellular matrix that induces partial regeneration of adult mammalian skin," Proc. Natl Acad. Sci. USA, vol. 86, pp. 933-937, Developmental Biology (Feb. 1989).
Yannas, Ioannis V., Ph.D., "Studies on the biological activity of the dermal regeneration template," Wound Repair and Regeneration, vol. 6, No. 6, pp. 518-523 (Nov.-Dec. 1998).
Concordia Medical, "BIOFELT® Tissue Engineering Scaffolds" (prior to Jun. 2008).
Jungkim, S., et al., "External trabeculectomy with T-Flux implant," European Journal of Ophthalmology, vol. 16, No. 3, pp. 416-421 (2006).
Kim, C., et al., "Clinical experience of a PTFE membrane implant surgery for refractory glaucoma," British Journal of Ophthalmology, vol. 87, pp. 63-70 (2003).
Raviv, Tal, M.D., et al., "Pericardial Patch Grafts in Glaucoma Implant Surgery," J. Glaucoma, vol. 7, No. 1, pp. 27-32 (1998).
Schreyger, Frank, et al., "SKGEL® Implant Versus T-Flux® Implant in the Contralateral Eye in Deep Sclerectomy with Phacoemulsification: Long-Term Follow-Up," The Open Ophthalmology Journal, vol. 2, pp. 57-61 (Mar. 2008).
"Tutoplast® Ophthalmic Patch Grafts," brochure, IOP Ophthalmics (2011).
"Tutoplast Orbital Implant Wraps—Tutoplast® Sclera," brochure, IOP Ophthalmics (2011).
Yannas, I.V., et al., "Design Principles and Preliminary Clinical Performance of an Artificial Skin," Biomaterials: Interfacial Phenomena and Applications, American Chemical Society, Advances in Chemistry Series, No. 199, pp. 475-481 (1982).
Zelefsky, Joseph R., et al., "Biodegradable collagen matrix implant for trabeculectomy," Expert Rev. Ophthalmology, vol. 3, No. 6, p. 613-617 (Dec. 2008).
Moster, Marlene R., et al., "Pericardial Patch Melting," Glaucoma Today, Surgical Pearls, pp. 29-31 (Sep./Oct. 2004).
OculusGen™ pamphlet, "Biodegradable Collagen Matrix Implant for glaucoma & selected ophthalmic surgeries" (Aug. 2006).
Ologen™ pamphlet, "Collagen Matrix for glaucoma & selected ophthalmic surgeries" (Apr. 2009).

* cited by examiner

METHOD OF USING A FIBER MATRIX FOR MAINTAINING SPACE IN SOFT TISSUES

CROSS-REFERENCE TO RELATED APPLICATION

The present application claims priority to U.S. provisional application Ser. No. 61/220,393, filed Jun. 25, 2009, the disclosure of which is incorporated herein by reference in its entirety.

FIELD OF THE INVENTION

The invention relates to maintaining space in soft tissues, such as maintaining space for drainage of aqueous humor from the eye to treat glaucoma.

BACKGROUND OF THE INVENTION

In various medical applications, it may be desired to maintain space in soft tissues. One such example is maintaining space for drainage of aqueous humor from the eye to treat glaucoma.

Glaucoma is an eye condition typically characterized by an increase in the intraocular pressure (IOP) of the eye to an abnormal level. A normal eye maintains a proper IOP by the circulation within the eye of aqueous humor. Aqueous humor is secreted from the ciliary body, passes through the pupil into the anterior chamber of the eyeball, and is filtered out of the eyeball via the trabeculum and the Canal of Schlemm (or Schlemm's Canal). With glaucoma, the aqueous humor excretory pathway is blocked, the aqueous humor cannot pass out of the eyeball at an adequate rate, the IOP rises, the eyeball becomes harder, and the optic nerve atrophies due to the pressure applied on its fibers leaving the retina. A characteristic optic neuropathy develops, resulting in progressive death of the ganglion cells in the retina, restriction of the visual field, and eventual blindness. Advanced stages of the disease are characterized also by significant pain.

Glaucoma treatment, if initiated early in the course of the disease, can prevent further deterioration and preserve most of the ocular functions. The goal of glaucoma treatment is to reduce the IOP to a level which is considered safe for a particular eye, but which is not so low as to cause ocular malfunction or retinal complications.

In the past, procedures and devices have been developed and implemented for providing an alternate route for aqueous humor to pass out of the eye. For example, in full thickness filtration surgery, a fistula is created through the limbal sclera, connecting directly the anterior chamber of the eyeball and the sub-conjunctival space. This provides an alternate route, allowing the aqueous humor to exit the anterior chamber of the eyeball through the fistula in the limbal sclera and to pass into the sub-conjunctival space. During healing, however, there is potential for cell growth and scar formation in the sclera and/or conjunctiva, potentially obstructing the fluid passage.

In guarded filtration surgery (trabeculectomy), a fistula created through the limbal sclera is protected by an overlying partial thickness sutured scleral flap. This procedure similarly provides an alternate route, allowing the aqueous humor to exit the anterior chamber of the eyeball, through the fistula in the limbal sclera, allowing the aqueous humor to pass under the scleral flap and into the sub-conjunctival space. Again there is a possibility of obstructing the fluid passage, due to the potential for cell growth and scar formation in the sclera and/or conjunctiva.

In a deep sclerectomy, a superficial flap is made in the sclera and then a second deep scleral flap is created and excised leaving a scleral reservoir or well under the first flap. A thin permeable membrane is exposed between the anterior chamber and the scleral reservoir. The procedure is non-penetrating in that no penetration is made into the anterior chamber. The aqueous humor percolates from the anterior chamber through the thin membrane into the scleral reservoir and into the Schlemm's Canal. This procedure can be difficult to perform and has not been shown to be fully effective in reducing IOP.

Trabeculoplasty procedures are procedures wherein a physician uses a laser to create holes in the trabecular meshwork in order to allow flow from the anterior chamber into the Schlemm's Canal. The two primary types of trabeculoplasty are argon laser trabeculoplasty (ALT) and selective laser trabeculoplasty (SLT). Trabeculoplasty may not be a suitable long-term treatment as the meshwork may close again, for example due to scarring.

The TRABECTOME® device of NeoMedix, Inc., has been proposed for another method for providing passage through the trabecular meshwork. The device is passed through a corneal incision and across the anterior chamber. The device's tip has a bipolar micro-electrocautery electrode that ablates and removes a strip of trabecular meshwork. As with trabeculoplasty, this procedure may not be a suitable long-term treatment as the meshwork may close again.

In addition to various procedures, drainage implant devices also have been developed and implemented. For example, some implants have a tube that is inserted through the limbal sclera. The tube provides an alternate route for the aqueous humor to leave the eye.

Many of these known devices and methods do not provide adequate regulation of IOP. For example, with some devices and methods, the initial procedure can cause excessive loss of aqueous humor from the eyeball during the early postoperative period, frequently leading to hypotony. With other devices and methods, there may be too much resistance to the flow of aqueous humor from the eyeball, thereby resulting in higher eventual IOP and an increased risk of late failure. There is also the risk that the drainage pathway will become clogged due to scarring, or that infection could occur because of the passageway into the eye. In certain valved implant devices, defects in and/or failure of the valve mechanisms can lead to either too much or too little aqueous humor exiting the eye. In procedures that drain into a "bleb" in the sub-conjunctival space, there is sometimes a risk of leakage or infection.

There continues to be a desire for improvements in treating glaucoma, to provide improved patient outcomes in an efficient manner.

In addition, there is a need for the ability to maintain space in soft tissues for glaucoma treatment and other applications.

SUMMARY OF THE INVENTION

The invention provides the ability to maintain space in soft tissues.

In accordance with some embodiments of the invention, a fiber matrix is provided for use in maintaining space in soft tissues, wherein the fiber matrix comprises a plurality of crossing fibers forming a mesh with a plurality of void spaces, and the fiber matrix is adapted to be implanted in contact with soft tissue. The fibers and void spaces are sized and arranged so as to permit passage of fluid through the fiber matrix and to inhibit formation of scar tissue through the fiber matrix.

In accordance with some embodiments of the invention, the fiber matrix is provided for use in treatment of glaucoma, wherein the fiber matrix has a generally planar shape, wherein the fiber matrix is adapted to be implanted in contact with scleral tissue, and wherein the fibers and void spaces are arranged so as to permit passage of aqueous humor through the fiber matrix.

In accordance with some embodiments of the invention, the fibers of the fiber matrix are non-woven. The fibers may comprise a polymeric material. The fiber matrix may be manufactured by electrospinning. The fibers may comprise a biostable and/or a biodegradable material. For example, the fibers may be made of a biostable fluoropolymer, such as polyvinylidene difluoride (PVDF). As another example, the fibers may be made of a biodegradable polymer, such as a copolymer of polylactic acid and polyglycolic acid (PLGA). The fiber matrix may comprise a first set of fibers formed of a biostable material and a second set of fibers formed of a biodegradable material. Additionally or alternatively, a biodegradable material may be added to the fiber matrix and/or coated over the fiber matrix to at least partially impede passage of fluid through the fiber matrix until degradation of the biodegradable material.

A fiber matrix in accordance with the invention may be suitably sized for a desired glaucoma treatment procedure. For example, the generally planar shape of the fiber matrix may be between about 1 mm and about 15 mm in its longest dimension and between about 1 mm and about 10 mm in its shortest dimension, although other dimensions are possible. The generally planar shape may have a thickness between about 25 microns and about 150 microns, although other dimensions are possible. The generally planar shape of the fiber matrix may have a radius of curvature approximating a radius of curvature of the scleral tissue. For example, the generally planar shape of the fiber matrix may have a radius of curvature of about 12 mm.

The fibers may have a thickness between about 10 nanometers and about 100,000 nanometers, although other dimensions are possible. The fiber matrix may have a porosity of about 25% to about 95%. The fiber matrix may have a permeability of about 10 mm per square cm per minute to about 300 mm per square cm per minute. The fiber matrix may have suture holes for securing the fiber matrix to the soft tissue by sutures.

In accordance with some embodiments of the invention, the fiber matrix may comprise an upper portion, a lower portion, and a pocket between the upper portion and the lower portion for receiving a scleral flap. In accordance with some embodiments of the invention, a permeable polymer anchor may be affixed to the fiber matrix, with the permeable polymer anchor adapted to allow for ingrowth of cells to secure the fiber matrix to the soft tissue. In accordance with some embodiments of the invention, a stretchable polymer may cover the crossing fibers and void spaces such that pressure from aqueous humor causes the stretchable polymer to stretch in order to facilitate passage of aqueous humor through the stretchable polymer. In accordance with some embodiments of the invention, one or more frame elements may be utilized. A suitable therapeutic agent may be carried by the fiber matrix.

In some embodiments of the invention, the invention is directed to the use of fibrous material in the manufacture of a product for treatment of glaucoma. The manufacturing steps comprise arranging the fibrous material into a fiber matrix comprising a plurality of crossing fibers forming a mesh with a plurality of void spaces, wherein the fibers and void spaces are sized and arranged so as to permit passage of aqueous humor through the fiber matrix and so as to inhibit formation of scar tissue through the fiber matrix, and forming the fiber matrix into a generally planar shape and into a size and shape adapted to be implanted in contact with scleral tissue. The step of arranging the fibrous material into a fiber matrix may be done by electrospinning.

In some embodiments of the invention, the invention is directed to a method of using a fiber matrix in treatment of glaucoma. The method comprises performing a procedure for increasing the flow of aqueous humor from an eye and implanting a fiber matrix comprising a plurality of crossing fibers forming a mesh with a plurality of void spaces, wherein the fiber matrix, by the size and arrangement of the fibers and void spaces of the fiber matrix, permits passage of aqueous humor through the fiber matrix and inhibits formation of scar tissue through the fiber matrix.

The method may include, in the procedure for increasing the flow of aqueous humor from an eye, creating a scleral flap. The method may further comprise suturing the scleral flap to surrounding scleral tissue with at least part of the fiber matrix under the scleral flap, and this suturing may be done through suture holes in the fiber matrix. The method may further additionally or alternatively comprise suturing the fiber matrix to scleral tissue, and this suturing may be done through suture holes in the fiber matrix. The fiber matrix may be implanted such that all of the fiber matrix is located under the scleral flap, none of the fiber matrix is located under the scleral flap, or that part of the fiber matrix is located under the scleral flap and another part of the fiber matrix is located outside of the scleral flap. In a specific example, the scleral flap comprises at least three sides, the fiber matrix is implanted such that a part of the fiber matrix is located under the scleral flap and other parts of the fiber matrix extend outside of the scleral flap at each of the three sides, and the scleral flap is sutured to surrounding scleral tissue at locations between adjacent sides. In another specific example, the fiber matrix is implanted such that a part of the fiber matrix is located under the scleral flap and another part of the fiber matrix is located on top of the scleral flap.

In procedures without a scleral flap, the fiber matrix may be positioned at the outlet end of the flow passage, between the sclera and the conjunctiva of the eye. Additionally or alternatively, the procedure for increasing the flow of aqueous humor from an eye may include implanting a drainage device in the eye, and the fiber matrix may be implanted such that the fiber matrix covers at least a portion of the drainage device, between the portion of the drainage device and the conjunctiva of the eye.

In other methods, a fiber matrix comprising a plurality of crossing fibers forming a mesh with a plurality of void spaces is implanted such that the fiber matrix is adjacent soft tissue. By the size and arrangement of the fibers and void spaces of the fiber matrix, passage of fluid through the fiber matrix is permitted, and formation of scar tissue through the fiber matrix is inhibited. The fiber matrix may be used for maintaining a nerve tunnel, for maintaining a tendon tunnel, for treating wrinkles, and/or for separating tissues in surgery.

The above summary is not meant to be limiting. The invention is defined by the claims appended hereto. Example embodiments are provided in the accompanying drawings and described in the detailed description given below. These are provided as examples only, as other embodiments of the invention are also within the scope of the appended claims.

DETAILED DESCRIPTION

Figure 1:
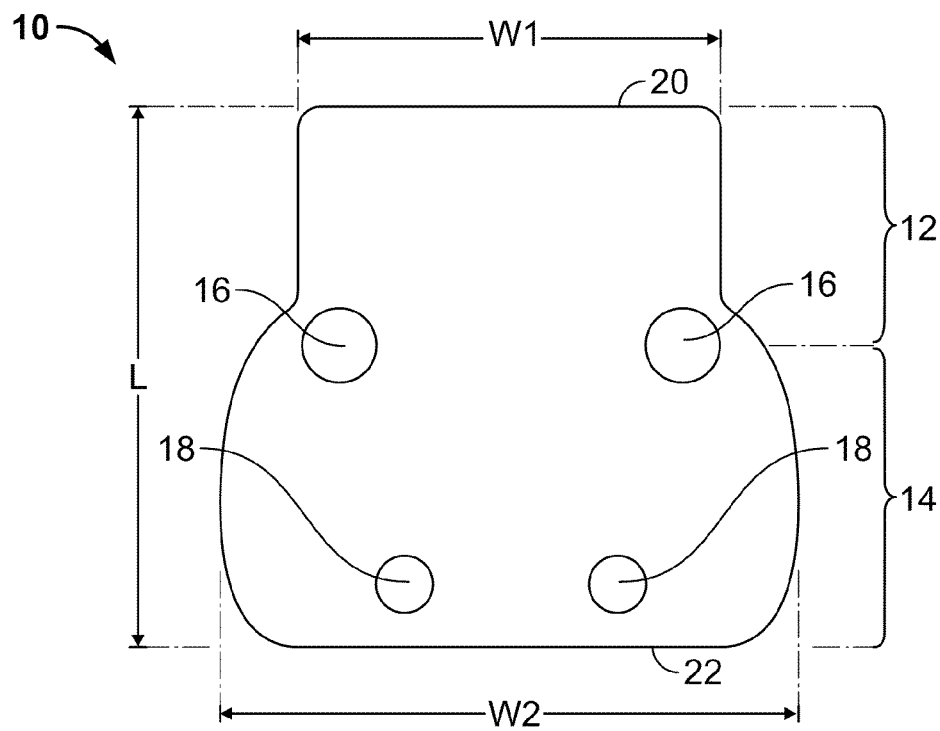
FIG. 1 illustrates an example of a fiber matrix in accordance with an embodiment of the invention.

FIG. 1 illustrates an example of a fiber matrix 10 in accordance with an embodiment of the invention. The fiber matrix 10 comprises a plurality of fibers, as described in more detail below with reference to FIG. 2.

The fiber matrix 10 has a generally planar shape, with the term "generally planar" being used here to include flat planar shapes as well as shapes that follow a curved surface area, such as the surface of an eye. For example, the generally planar shape may be curved to have a radius of curvature approximating a radius of curvature of scleral tissue of an eye where the fiber matrix 10 is intended to be implanted.

The fiber matrix 10 illustrated in FIG. 1 has a leading edge 20, a leading portion 12, a trailing edge 22, and a trailing portion 14. As described in more detail below, the leading portion 12 is intended to be implanted under a scleral flap, and the trailing portion 14 is intended to be implanted on top of the sclera, outside of the scleral flap but under the conjunctiva of the eye.

The size of the fiber matrix 10 may of course vary depending upon the particular application. However, as an example, in the case of a scleral flap with a width of about 4 mm, the width W1 of the leading portion 12 may be about 5-6 mm, so that most of this width is under the scleral flap after implantation. In the fiber matrix 10 as shown, the width gradually increases in a transition area between the leading portion 12 and the trailing portion 14. At its largest width in the example shown, the width W2 of the trailing portion 14 may be about 7-8 mm. The length L of the fiber matrix 10 may be, for example, about 9 mm. Of course, many other shapes and dimensions for the fiber matrix 10 are possible. For example, the generally planar shape of the fiber matrix may be between about 1 mm and about 15 mm in its longest dimension and between about 1 mm and about 10 mm in its shortest dimension.

The fiber matrix 10 has a thickness suitable for implantation of the leading portion 12 under a scleral flap and for implantation of the trailing portion 14 under the conjunctiva. For example, the thickness of the fiber matrix may be between about 25 microns and about 150 microns, but thicknesses outside of this range are also possible depending upon the desired application.

The fiber matrix 10 in FIG. 1 is illustrated with four suture holes 16, 18 for securing the fiber matrix 10 to the scleral tissue by sutures. In this embodiment, two suture holes 16 are located in the transition area between the leading portion 12 and the trailing portion 14, and two suture holes 18 are located near the trailing edge 22 of the fiber matrix.

The corners of the fiber matrix may be rounded to reduce the possibility of eye irritation or injury that may be attributable to sharp corners. In the example illustrated in FIG. 1, the two corners at the trailing edge 22 are rounded.

Figure 2:
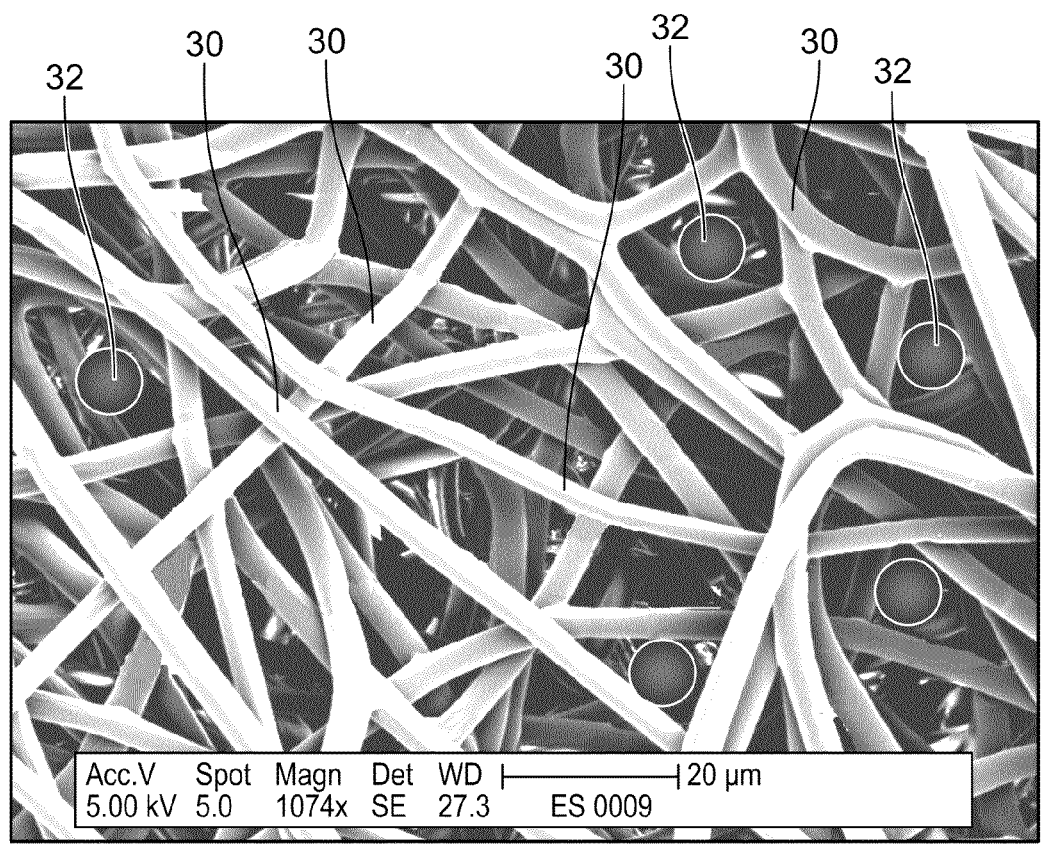
FIG. 2 illustrates a magnified view of fibers of a fiber matrix in accordance with an embodiment of the invention.

FIG. 2 illustrates a magnified view of a fiber matrix, such as the fiber matrix 10, in accordance with an embodiment of the invention. As can be seen in FIG. 2, the fiber matrix comprises a plurality of crossing fibers 30 forming a mesh with a plurality of void spaces between the fibers 30. The fibers 30 and void spaces are sized and arranged so as to permit passage of aqueous humor through the fiber matrix and to inhibit formation of scar tissue through the fiber matrix, as described below.

The fibers may have a thickness between about 10 nanometers and about 100,000 nanometers, but other thicknesses are possible depending on the application. In the embodiment illustrated in FIG. 2, the fibers have a thickness between about 3 microns and about 5 microns (i.e., between about 3000 nanometers and about 5000 nanometers). Because of the size and arrangement of the fibers, there are substantially no or very few through passages extending all of the way through the thickness of the fiber matrix that are large enough to allow formation of scar tissue. For illustration, schematic views of cells 32 of about 7 microns in size are shown in FIG. 2. As can be seen, the fibers 30 block passage of the cells 32 through the fiber matrix.

The fibers 30 of the fiber matrix may be made of any suitable material. For example, the fibers in the embodiment of FIG. 1 are polymer fibers, but fibers of other materials such as biocompatible metal or ceramic fibers may be used. The fibers may be biostable, or they may be biodegradable. As one example, the fibers may be made of a fluoropolymer such as polyvinylidene difluoride (PVDF), a biostable material. As another example, the fibers may be made of a copolymer of polylactic acid and polyglycolic acid (PLGA), a biodegradable material. Combinations of biostable and biodegradable materials also may be used, as described in more detail below.

The term "fiber" as used herein is not limited to any particular cross-section. The cross-section of the fibers may be, for example, circular, elliptical, square, rectangular, or any other suitable shape. With a rectangular or other similar cross-section, for example, the fibers may resemble flat strips.

In the manufacturing process, fibrous material is arranged into a fiber matrix comprising a plurality of crossing fibers forming a mesh with a plurality of void spaces. The fibers and void spaces are sized and arranged so as to permit passage of aqueous humor through the fiber matrix and to inhibit formation of scar tissue through the fiber matrix, as described below. The fiber matrix may be suitably formed, either during arrangement of the fibers or in one or more subsequent manufacturing steps, into a generally planar shape and into a size and shape adapted to be implanted as described herein. In the example illustrated in FIGS. 1 and 2, the fibers of the fiber matrix are non-woven, i.e., they are neither woven nor knitted. The fibers are joined together by entanglement during manufacture and possibly, depending on the materials and manufacturing process used, by bonding such as by chemical cross-linking or thermal bonding. In the example illustrated in FIGS. 1 and 2, the fiber matrix is manufactured by electrospinning, resulting in a fiber matrix of polymeric fibers joined together by mechanical entanglement and chemical cross-linking.

The fiber matrix may be manufactured in layers of fibers. It will be appreciated that because of the three-dimensional nature of the matrix, the fibers at a particular layer or level may have relatively wide void spaces between them. Such void spaces at a particular layer or level, by themselves, may not alone be sufficient to prevent the passage of cells for scar tissue formation. However, because of the fibers at other layers or levels, and their placement relative to the fibers at other layers or levels, the fiber matrix as a whole substantially avoids or minimizes through passages through the thickness of the fiber matrix, in a manner that inhibits (i.e., reduces, minimizes, or substantially prevents) the passage of cells for scar tissue formation. This can be seen in FIG. 2, in which the cells 32 may be able to pass partway into the matrix, but are inhibited from passing through the matrix.

The porosity of the matrix can be measured as the percentage of the volume of the overall fiber matrix that is composed of void spaces as opposed to fibers. For example, the fiber matrix of FIG. 1 has an overall volume based on its outer dimensions (overall shape). However, the internal volume comprises fibers as well as void spaces between the fibers. The fibers themselves may take up anywhere from a small percentage to a large percentage of the overall volume, e.g., from about 5% to about 75% of the overall volume. Accordingly, the porosity of the matrix may range from about 95% to about 25%, but other porosities are possible depending on the application. When the fiber matrix has a relatively high porosity, the amount of fibers actually contacting tissue is minimized, leading to a more inert overall matrix.

It will be appreciated from the above description that a fiber matrix in accordance with embodiments such as those described above will permit omnidirectional flow of aqueous humor through the matrix, i.e., flow in all directions. The permeability of the fiber matrix is dependent on the materials, geometry and arrangement of the fibers. The material, geometry and arrangement of fibers can be tailored as desired to the characteristics of the particular application, such as, for example, the pressures, desired flow rates, type of procedure being performed, etc.

Figure 3A:
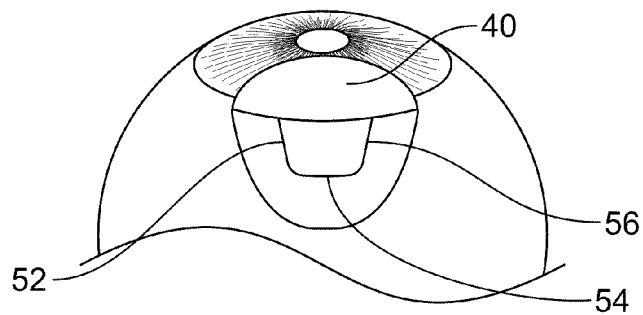
FIGS. 3A-3D illustrate steps in an example of a method of implanting a fiber matrix in accordance with an embodiment of the invention.
Figure 3B:
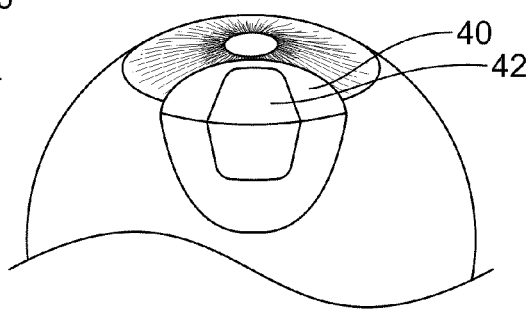

FIGS. 3A-3D illustrate steps in an example of a method of implanting a fiber matrix in accordance with an embodiment of the invention. In FIGS. 3A and 3B, a guarded filtration (trabeculectomy) procedure, well-known in the art for increasing the flow of aqueous humor from an eye, is performed. During the procedure, a conjunctival flap 40 and a scleral flap 42 are created, as is known in the art. The scleral flap 42 may be formed, for example, by three cut lines 52, 54, 56 as shown. The scleral flap is not limited to this shape; for example, the scleral flap may have a triangular shape formed by two cuts or a semicircular shape formed by one cut. Beneath the scleral flap, a piece of tissue in the drainage angle of the eye may be removed, creating a fistula or passageway connecting the anterior chamber of the eye to the space under the scleral flap.

Figure 3C:
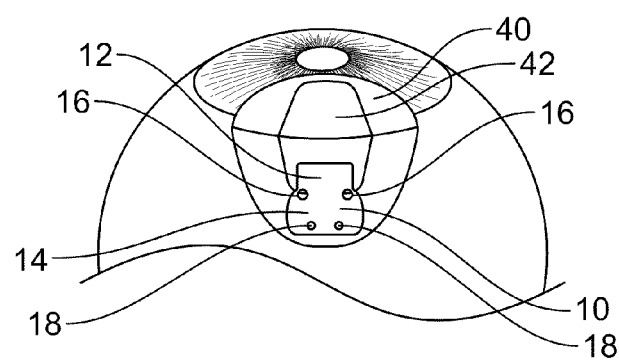

As shown in FIG. 3C, with the scleral flap 42 raised, a fiber matrix 10 in accordance with an embodiment of the invention is placed with its leading portion 12 positioned in the scleral well and with its trailing portion 14 positioned outside the scleral well. The two suture holes 16 are positioned at corners of the scleral well. The fiber matrix 10 may be handled and manipulated by forceps or another suitable instrument.

Figure 3D:
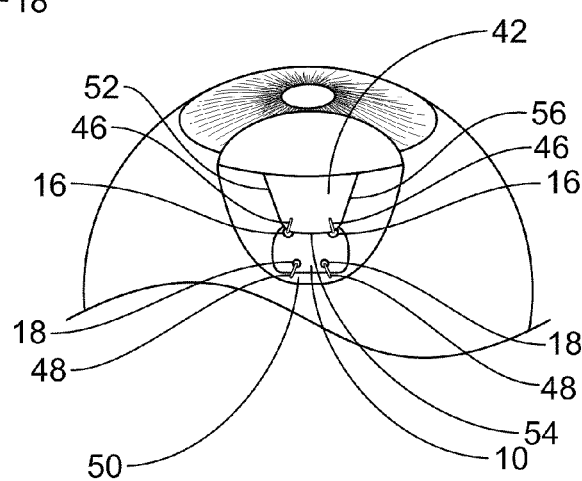

After the fiber matrix 10 is suitably positioned, the scleral flap 42 is placed back into position, as shown in FIG. 3D. The scleral flap is then sutured to surrounding scleral tissue 50 by sutures 46 passing through suture holes 16 in the fiber matrix 10, with part of the fiber matrix 10 secured under the scleral flap. The trailing portion 14 of the fiber matrix 10, which lies in contact with scleral tissue 50 outside of the scleral flap 42, is sutured to surrounding scleral tissue 50 by sutures 48 passing through suture holes 18 in the fiber matrix 10. The conjunctival flap is then placed back into position, and it may be suitably sutured as well.

Once implanted, the fiber matrix 10 functions to permit passage of aqueous humor through the fiber matrix and to inhibit formation of scar tissue. Thus, the aqueous humor flowing out of the anterior chamber into the scleral well passes through the fiber matrix 10 and out of the scleral well, underneath the conjunctiva.

Depending on the application and the materials, geometry and arrangement of the fibers and the fiber matrix, the fiber matrix may initially impede flow and subsequently permit increased flow. In the short period following glaucoma surgery, it can be very important to avoid excessive outflow and maintain a minimal IOP. Failure to do this can result in hypotony and potentially serious complications. The fiber matrix can be designed to serve as a liquid barrier in the short term following surgery. In an example construction, in the presence of liquid like water, an irrigating solution, or aqueous humor, the small fibers of the fiber matrix can have the ability to resist liquid flow through the fiber matrix. For example, with a relatively dense fiber matrix, due to the surface tension of the liquid, the fiber matrix can initially resist penetration of the fluid into the volume of the fiber matrix. Such a fiber matrix can have the ability to hold an air reservoir (bubble) within the fiber matrix, even though the fiber matrix is not a closed body. As long as the fluid does not flow into the fiber matrix, the fiber matrix will act as a barrier to liquid flow (although some flow may occur around the matrix). As time passes, the air inside the fiber matrix will naturally dissolve into the surrounding liquid, and liquid will take its place. At this stage flow will increase through the fiber matrix.

The pressure of the liquid against the fiber matrix also can affect whether and how long the fiber matrix acts as a barrier to flow. In the presence of a high pressure gradient, such as from large internal eye pressure, the surface tension will more easily break and fluid will flow more easily into the fiber matrix volume. Thus, for patients with higher IOP, it may be desirable to select a fiber matrix with a higher resistance to flow, such as a denser fiber matrix.

The property of changing states, from a barrier to a flow device, is closely related to the general characteristics of the fiber matrix. These characteristics include: (1) fiber density (as the density increases, the pressure resistance increases), (2) type of material for the fibers (hydrophobic materials generally will hold a higher surface tension than hydrophilic materials), and (3) fiber thickness (for two materials with the same general porosity, as the fiber diameter becomes smaller, the matrix would hold a higher surface tension and higher pressure).

The property of changing states, from a barrier to a flow device, can additionally or alternatively be accomplished through the use of biodegradable materials. For example, some or all of the fibers in the fiber matrix can be biodegradable. As another example, a biodegradable filler material may be provided within the fiber matrix. As another example, the matrix may have multiple layers in which one or more of the layers is a layer of biodegradable material (porous or non-porous) or fibers. In such cases, the biodegradable material or fibers initially helps provide a barrier to flow. Over time, the biodegradable material dissolves, thereby increasingly permitting more flow until the biodegradation is complete.

Again with reference to FIG. 3D, while the implanted fiber matrix 10 permits passage of aqueous humor and inhibits formation of scar tissue, the fiber matrix 10 also inhibits the scleral flap 42 from reattaching to its base. In addition, because the fiber matrix 10 extends from inside the scleral well to outside the scleral well at cut lines 52, 54, 56 where the scleral flap 42 was cut from the surrounding scleral tissue 50, the fiber matrix helps prevent the scleral flap from reattaching to the surrounding sclera 50 along these lines. Thus, the fiber matrix 10 keeps the passageways at cut lines 52, 54, 56 open to facilitate passage of aqueous humor from underneath the scleral flap. The portion of the fiber matrix placed on top of the sclera can help prevent scar tissue formation between the conjunctiva and the sclera.

In the embodiment illustrated in FIGS. 3A-3D, the scleral flap 42 comprises three sides, formed at cut lines 52, 54, 56, and the fiber matrix 10 is implanted such that a part of the fiber matrix is located under the scleral flap 42 and other parts of the fiber matrix extend outside of the scleral flap 42 at each of the three sides. The scleral flap 42 is sutured to surrounding scleral tissue 50 at locations between adjacent sides. Of course, alternatives are possible in which the fiber matrix extends out of the scleral well at only one side or more than one side, or in which the fiber matrix is implanted such that all of the fiber matrix is located under the scleral flap. Similarly, when the scleral flap has another shape, such as triangular, semicircular, etc., the fiber matrix may extend out of the scleral well at one or more cut lines or may be completely within the scleral well.

The geometry of the fiber matrix may be adjusted not just to inhibit scar formation at desired locations as described above, but also to disperse the aqueous humor. Thus, in FIG. 3D, the aqueous humor is dispersed out from under the scleral flap 42 at each of the cut lines 52, 54, 56. In addition, because the trailing portion 14 is wider than the leading portion 12 as illustrated in FIG. 1, the trailing portion helps disperse the aqueous humor over a wider area.

It will be appreciated that when the fiber matrix is biostable, it will remain in position to continue to facilitate flow. In the case of a fiber matrix made of biodegradable material, it will biodegrade over time. The material may be selected so that the fiber matrix stays in place long enough during the healing process to allow healing to take place while maintaining the flow passages intact. Thus, for example, the scleral flap will have healed substantially unattached to its base, and with the cut lines open. Accordingly, even after the fiber matrix has biodegraded, the scleral well and the passages out of the scleral well remain viable. The material for biodegradation may be selected according to the desired biodegradation time. For example, the fiber matrix may biodegrade within about 6 months, within about 3 months, or in any other suitable amount of time.

The materials, fiber arrangement, and geometry of the fiber matrix all can be adjusted in order to achieve the particular desired result. The healing process of the tissue occurs generally in three phases. The first phase, inflammation, occurs within several days following the procedure. The second phase, proliferation, can last for several weeks following the inflammation. The third phase, remodeling, follows the proliferation and can take several months.

The material of the fiber matrix can be selected to minimize the tissue reaction. As mentioned above, the fibers may be biostable, biodegradable, or a combination thereof. The fiber matrix may be designed such that the material in contact with tissue at implantation is substantially inert to reduce the reaction, and thereby reduce the cell migration and growth factors.

The micro-structure of the fiber matrix can be selected to reduce tissue response by minimizing the interface between the material and the surrounding tissue. With much of the matrix volume comprised of void spaces, the contact of fibers with the tissue can be minimized. The micro structure also controls the penetration of cells into the volume of the matrix and assists in the formation of new tissue surrounding the matrix. During the inflammation phase, thin fibers decrease the cell migration, while in the proliferation phase, the fibers assist in directing the proliferated cells to a preferred location. This can be done by designing the distance between fibers in such a way that cells are not able to penetrate significantly into the implant, as described above.

The macro-structure of the fiber matrix can be tailored to the particular application. With a material that is soft and flexible, it is very easy to shape it according to any desired pattern. It is possible to cut the fiber matrix during the manufacturing process and provide it in its final shape. Another option is that the product can be provided to a physician in a general shape and size, and the physician can shape the fiber matrix into its final figure and geometry according to need.

It will be appreciated that a fiber matrix in accordance with the invention can improve available treatments of glaucoma. In trabeculectomy procedures, a bleb is formed from the flow of aqueous humor under the conjunctiva. In addition, drugs are sometimes used, such as anti-metabolite drugs (MMC, 5FU). The use of a fiber matrix as described herein can enable maintenance of the bleb while avoiding complications sometimes associated with such drugs.

Figure 4A:
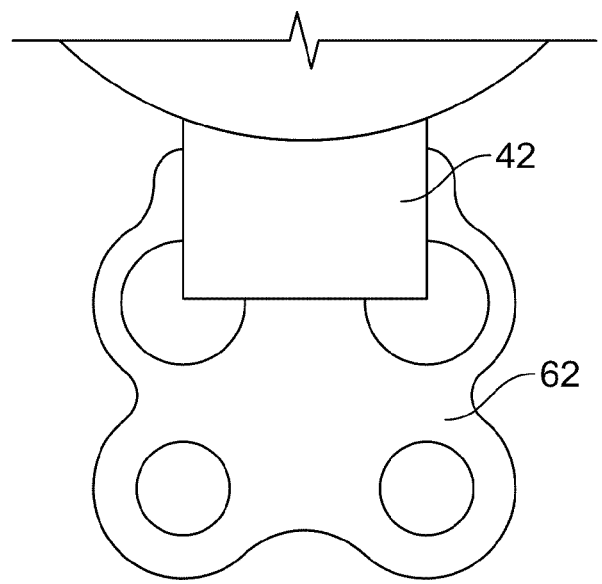
FIGS. 4A-4C illustrate some other examples of fiber matrices in accordance with other embodiments of the invention.
Figure 4B:
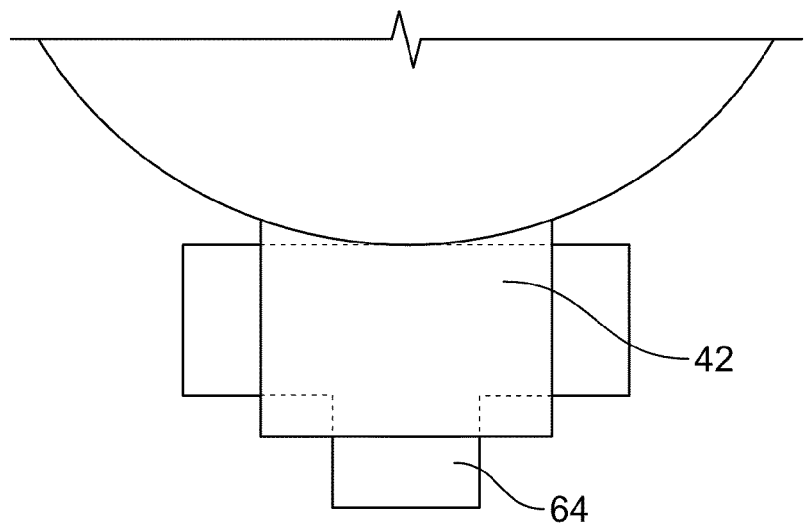
Figure 4C:
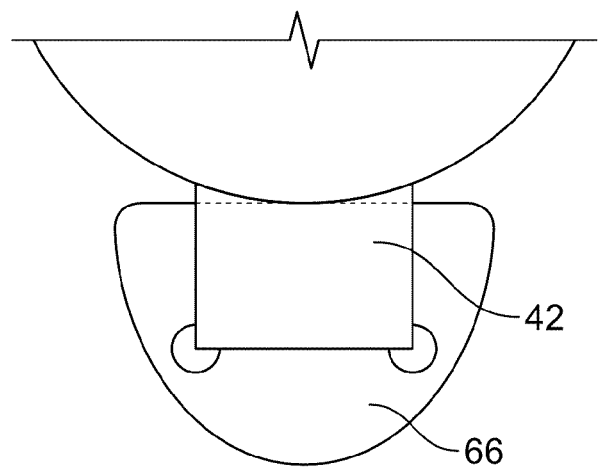

FIGS. 4A-4C illustrate some other examples of fiber matrices in accordance with other embodiments of the invention, showing alternative geometries. FIG. 4A shows a fiber matrix 62 having a rounded pattern with larger suture holes. FIG. 4B shows a fiber matrix 64 with three wings for extending out from under the three sides of the scleral flap 42. FIG. 4C shows a fiber matrix 66 having a generally semi-elliptical shape. These are only examples, as many other size and shape variations are of course possible.

In addition to the procedure discussed above wherein at least a part of the fiber matrix is implanted under a scleral flap, it is also possible to implant the fiber matrix such that at least a part of the fiber matrix is located on top of the scleral flap, with no part of the fiber matrix under the scleral flap. In this way, the fiber matrix is implanted at the outlet end of the flow passage, between the sclera and the conjunctiva. The fiber matrix can help prevent scar tissue formation between the cut areas at the edges of the scleral flap cup and the conjunctiva.

In addition, it is possible to use a fiber matrix in conjunction with other procedures for increasing the flow of aqueous humor from an eye. For example, in the case of a full thickness fistula with no scleral flap, the fiber matrix may be implanted such that the fiber matrix is at the outlet end of the fistula flow passage, again between the sclera and the conjunctiva of the eye. As another example, the procedure may include implanting a drainage device in the eye, such as one of the drainage devices known in the art. The fiber matrix may be implanted such that the fiber matrix covers at least a portion of the drainage device, between the portion of the drainage device and the conjunctiva of the eye. This will inhibit the formation of scar tissue that otherwise may be caused in response to the drainage device. This type of implantation may reduce the risk of conjunctival erosion related with the implantation of drainage devices.

Figure 5:
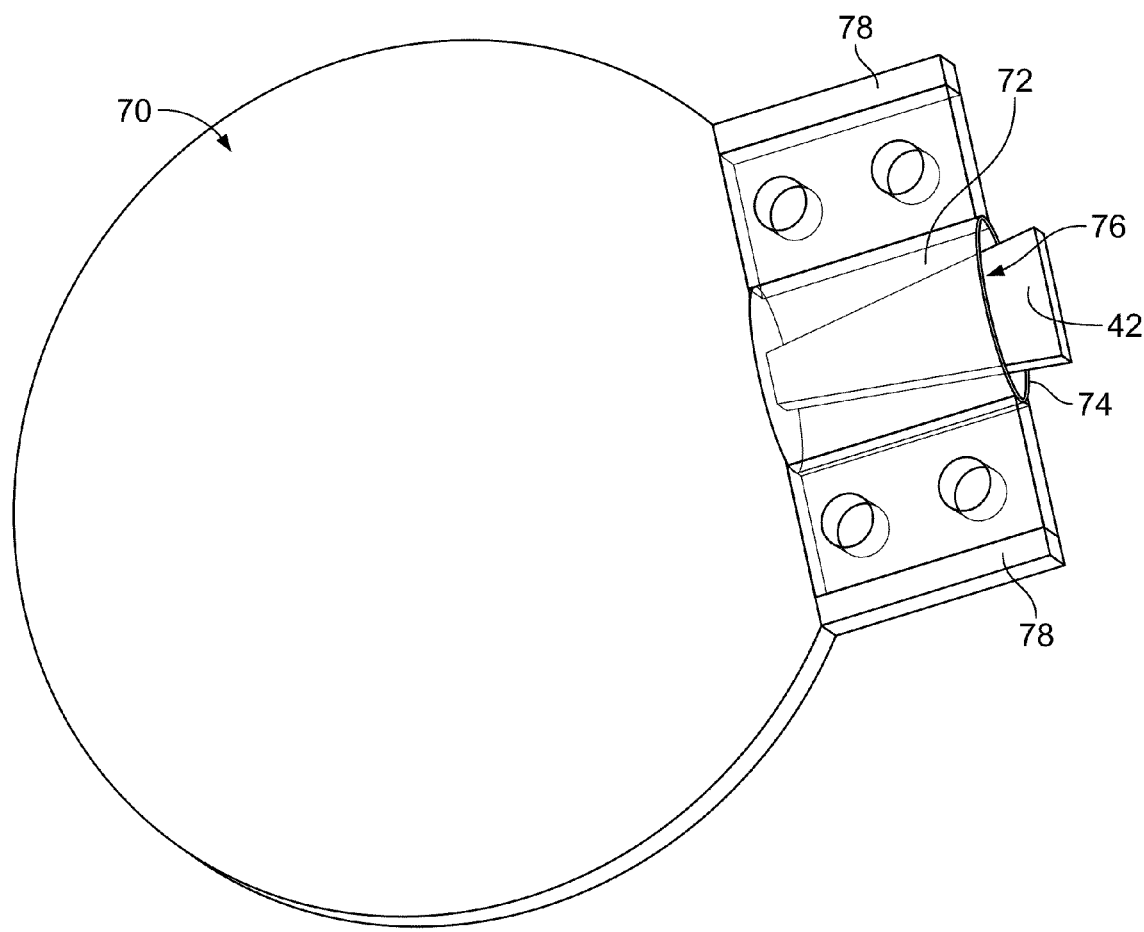
FIG. 5 illustrates an example of a fiber matrix in accordance with another embodiment of the invention, the fiber matrix comprising an upper portion, a lower portion, and a pocket between the upper portion and the lower portion for receiving a scleral flap.

FIG. 5 illustrates an example of a fiber matrix 70 in accordance with another embodiment of the invention. The fiber matrix 70 comprises an upper fiber matrix portion 72, a lower fiber matrix portion 74, and a pocket 76 between the upper fiber matrix portion 72 and the lower fiber matrix portion 74. The pocket is sized and shaped for receiving a scleral flap 42, as illustrated in FIG. 5. With the fiber matrix 70 implanted as illustrated in FIG. 5, the fiber matrix 70 is implanted such that a part of the fiber matrix is located under the scleral flap and another part of the fiber matrix is located on top of the scleral flap. Thus, the fiber matrix can assist flow as described above and can inhibit scar formation between the scleral flap and its base, at the cut edges of the scleral flap, and between the scleral flap and the conjunctiva. In addition, because the fiber matrix is held in place by the positioning of the scleral flap in the pocket 76, the matrix may be implanted with or without sutures. The fiber matrix 70 illustrated in FIG. 5 is shown with two permeable polymer anchors 78 adapted to allow for ingrowth of cells to help secure the fiber matrix 70 to the scleral tissue.

Figure 6:
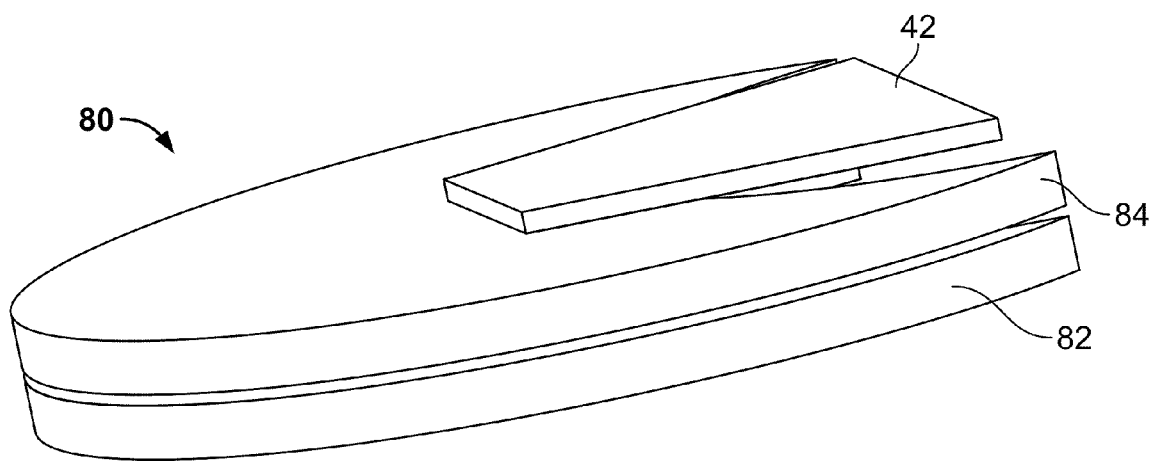
FIG. 6 illustrates an example of a fiber matrix in accordance with another embodiment of the invention, with a stretchable polymer covering the fiber matrix.

FIG. 6 illustrates an example of another embodiment 80 of the invention. This embodiment includes a fiber matrix 82 in combination with a stretchable polymer 84 covering the fiber matrix 82. When aqueous humor penetrates the fiber matrix 82, it puts pressure on the stretchable polymer 84, causing it to stretch and expand. As it does so, it becomes more permeable, facilitating passage of aqueous humor through the stretchable polymer. In this way, more flow is inhibited initially, but over time and with increased pressure, more flow is permitted. When the pressure subsides, the polymer 84 contracts again. In this way, the polymer 84 acts as a pressure-regulating valve.

Figure 7:
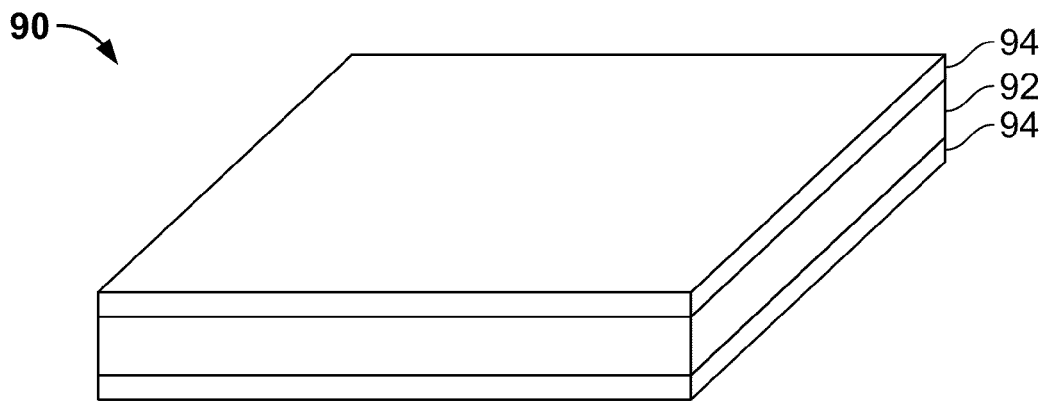
FIG. 7 illustrates an example of a fiber matrix in accordance with another embodiment of the invention, with a biodegradable coating layer over the crossing fibers and void spaces.

FIG. 7 illustrates an example of another embodiment 90 of the invention. In this embodiment, a fiber matrix 92 is provided with a biodegradable coating layer 94 over each of its top and bottom surfaces. The material of each biocompatible coating layer 94 can be substantially inert to reduce reaction. When the fiber matrix is initially implanted, the coating layers 94 substantially inhibit flow. However, over time, as the biodegradable coating layers 94 erode, more flow is permitted.

As discussed above, another embodiment with a similar ability to allow increased flow over time is a fiber matrix comprising a first set of fibers formed of a biostable material and a second set of fibers formed of a biodegradable material. Over time, as the biodegradable fibers erode, more flow is permitted. In yet another embodiment with a similar ability to allow increased flow over time, a fiber matrix is made of fibers formed of a biostable material, and the fiber matrix is impregnated with a biodegradable material. Over time, as the biodegradable material erodes, more flow is permitted. In each of these embodiments with biodegradable material, the biodegradable material at least partially impedes passage of aqueous humor through the fiber matrix until the degradation of the biodegradable material.

While FIG. 7 illustrates a fiber matrix 92 with top and bottom biodegradable coating layers 94, other arrangements of layers are possible. The fiber matrix may be made with various combinations of layers of fibers of different materials and properties. For example, biostable fibers may be arranged in layers adjacent to biodegradable fibers. Other layers not made of fibers, such as biodegradable coatings or internal layers, may also be used.

Figure 8A:
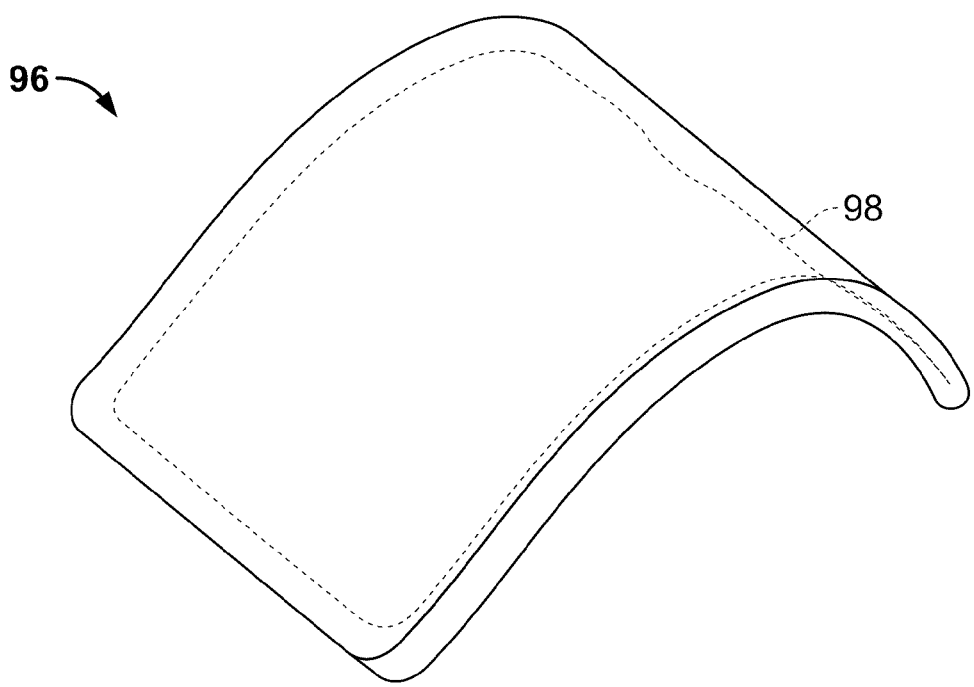
FIGS. 8A and 8B illustrate an example of a fiber matrix in accordance with another embodiment of the invention, with a frame element.
Figure 8B:

FIGS. 8A and 8B illustrate an example of a fiber matrix 96 in accordance with another embodiment. The fiber matrix 96 is provided in combination with a frame element 98. In this example, the frame element comprises a continuous wire frame extending around the periphery of the fiber matrix, embedded within the fiber matrix. The frame element aids in defining the periphery of the fiber matrix and can assist in manufacturing. It also can assist in maintaining the shape of the fiber matrix during implantation.

A fiber matrix as described herein may carry one or more therapeutic agents for elution to the surrounding tissue. For example, the fiber matrix may be coated, impregnated, or otherwise provided with an anti-metabolite or antibiotic or glaucoma-treating drug. The drug may release over time, for example with 90% of the drug being eluted within the first 6 months.

A fiber matrix as described herein may be used for a variety of applications. For example, certain procedures can involve cutting and suturing of a nerve tunnel. In such a case, a fiber matrix as described herein may be provided around or adjacent the nerve. The fiber matrix would help maintain the nerve tunnel space, for example by inhibiting scar tissue formation. The fiber matrix also could assist in growth of the nerve.

As another example, in the case of a tendon cut, there can be a risk of adhesion between the tendon and tendon sheath or tunnel at the incision location. A fiber matrix as described herein may be provided around or adjacent to the tendon. The fiber matrix would help maintain the tendon tunnel space and would inhibit adhesion. The inner surface of the fiber matrix may comprise a lubricious polymer, which can facilitate movement of the tendon during the healing process.

As another example, a fiber matrix as described herein may be used for treatment of wrinkles. The fiber matrix may be formed as a bundle of fibers in a generally linear geometry (such as a fine string or rope). The fiber matrix can be injected underneath a wrinkle and can inflate the tissue to soften or eliminate the wrinkle. The fiber matrix can be compressed for delivery and loaded into a needle-like delivery device. The fiber matrix can be ejected from the delivery device, and, upon implantation, the fiber matrix will expand. Additionally or alternatively, the fiber matrix can be made of hygroscopic material such that, upon implantation, the fiber matrix will expand.

As a further example, a fiber matrix as described herein may be used for tissue separation in surgical situations. For example, a fiber matrix may be placed between abdominal tissues or tissues desired to be separated during heart surgery procedures.

A fiber matrix as described herein can control scar tissue formation during healing in such a way that other applications are possible. For example, a fiber matrix as described herein can be used as a coating or encasement for breast implants to inhibit capsular formation by controlling scar tissue formation. The fiber matrix material can be graded in a direction away from the contents of the implant (e.g., silicone gel or saline), from substantially completely or 100% dense to hold the contents of the implant, to a less dense matrix with voids to incorporate into the surrounding tissue.

As will be appreciated by persons having ordinary skill in the art, the various embodiments described hereinabove are given by way of example only. Various changes, modifications and variations may be applied to the described embodiments without departing from the scope of the invention, as defined by the appended claims.

The invention claimed is:

1. A method of using a fiber matrix in treatment of glaucoma comprising:
   (i) performing a procedure for increasing the flow of aqueous humor from an eye, the procedure including creating a scleral flap;
   (ii) lifting the scleral flap to allow access to a scleral well beneath the scleral flap;

(iii) positioning a fiber matrix such that a first part of the fiber matrix is located in the scleral well and a second part of the fiber matrix is located outside of the scleral well, wherein the fiber matrix comprises a plurality of crossing fibers forming a mesh with a plurality of void spaces; and (iv) replacing the scleral flap such that the first part of the fiber matrix is implanted under the scleral flap and the second part of the fiber matrix is implanted outside of the scleral flap and on top of the sclera;

wherein the fiber matrix, by the size and arrangement of the fibers and void spaces of the fiber matrix, permits passage of aqueous humor through the fiber matrix and inhibits formation of scar tissue through the fiber matrix.

2. A method of using a fiber matrix in treatment of glaucoma as recited in claim 1, wherein the fiber matrix has a generally planar shape.

3. A method of using a fiber matrix in treatment of glaucoma as recited in claim 1, wherein the fibers are non-woven.

4. A method of using a fiber matrix in treatment of glaucoma as recited in claim 1, wherein the fibers comprise a polymeric material.

5. A method of using a fiber matrix in treatment of glaucoma as recited in claim 1, wherein the fiber matrix is manufactured by electrospinning.

6. A method of using a fiber matrix in treatment of glaucoma as recited in claim 1, wherein the fibers comprise a biostable material.

7. A method of using a fiber matrix in treatment of glaucoma as recited in claim 1, wherein the fibers comprise a fluoropolymer.

8. A method of using a fiber matrix in treatment of glaucoma as recited in claim 1, wherein the fibers comprise polyvinylidene difluoride (PVDF).

9. A method of using a fiber matrix in treatment of glaucoma as recited in claim 1, wherein the fibers comprise a biodegradable material.

10. A method of using a fiber matrix in treatment of glaucoma as recited in claim 1, wherein the fibers comprise a copolymer of polylactic acid and polyglycolic acid (PLGA).

11. A method of using a fiber matrix in treatment of glaucoma as recited in claim 1, wherein the fibers comprise a first set of fibers formed of a biostable material and a second set of fibers formed of a biodegradable material.

12. A method of using a fiber matrix in treatment of glaucoma as recited in claim 1, further comprising using a biodegradable material to at least partially impede passage of fluid through the fiber matrix until degradation of the biodegradable material.

13. A method of using a fiber matrix in treatment of glaucoma as recited in claim 2, wherein the generally planar shape of the fiber matrix is between about 1 mm and about 15 mm in its longest dimension and between about 1 mm and about 10 mm in its shortest dimension.

14. A method of using a fiber matrix in treatment of glaucoma as recited in claim 2, wherein the generally planar shape of the fiber matrix has a thickness between about 25 microns and about 150 microns.

15. A method of using a fiber matrix in treatment of glaucoma as recited in claim 2, wherein the generally planar shape of the fiber matrix has a radius of curvature approximating a radius of curvature of the scleral tissue.

16. A method of using a fiber matrix in treatment of glaucoma as recited in claim 1, wherein the fibers have a thickness between about 10 nanometers and about 100,000 nanometers.

17. A method of using a fiber matrix in treatment of glaucoma as recited in claim 1, wherein the fiber matrix has a porosity of about 25% to about 95%.

18. A method of using a fiber matrix in treatment of glaucoma as recited in claim 1, wherein the fiber matrix comprises suture holes for securing the fiber matrix.

19. A method of using a fiber matrix in treatment of glaucoma as recited in claim 2, wherein the fiber matrix comprises an upper portion, a lower portion, and a pocket between the upper portion and the lower portion for receiving the scleral flap.

20. A method of using a fiber matrix in treatment of glaucoma as recited in claim 1, further comprising using a permeable polymer anchor adapted to allow for ingrowth of cells to secure the fiber matrix.

21. A method of using a fiber matrix in treatment of glaucoma as recited in claim 2, further comprising using a stretchable polymer covering the crossing fibers and void spaces such that pressure from aqueous humor causes the stretchable polymer to stretch to facilitate passage of aqueous humor through the stretchable polymer.

22. A method of using a fiber matrix in treatment of glaucoma as recited in claim 1, further comprising using a biodegradable coating layer over the crossing fibers and void spaces.

23. A method of using a fiber matrix in treatment of glaucoma as recited in claim 1, further comprising using one or more frame elements.

24. A method of using a fiber matrix in treatment of glaucoma as recited in claim 1, further comprising using a therapeutic agent carried by the fiber matrix.

25. A method as claimed in claim 1, further comprising suturing the scleral flap to surrounding scleral tissue with the first part of the fiber matrix under the scleral flap.

26. A method as claimed in claim 1, further comprising suturing the scleral flap to surrounding scleral tissue through suture holes in the fiber matrix, with the first part of the fiber matrix under the scleral flap.

27. A method as claimed in claim 1, further comprising suturing the fiber matrix to scleral tissue.

28. A method as claimed in claim 1, further comprising suturing the fiber matrix to scleral tissue through suture holes in the fiber matrix.

29. A method as claimed in claim 1, wherein the scleral flap comprises at least three sides, wherein the fiber matrix is implanted such that the first part of the fiber matrix is located under the scleral flap and portions making up the second part of the fiber matrix extend outside of the scleral flap at each of the three sides, and further comprising suturing the scleral flap to surrounding scleral tissue at locations between adjacent sides.

30. A method as claimed in claim 1, wherein the fiber matrix is implanted such that the second part of the fiber matrix is located on top of the scleral flap.

31. A method as claimed in claim 1, wherein the step of performing a procedure for increasing the flow of aqueous humor from an eye includes, in addition to creating the scleral flap, creating a flow passage through the sclera of the eye.

32. A method as claimed in claim 31, wherein the fiber matrix is implanted such that the second part of the fiber matrix is located on top of a scleral flap.

33. A method of using a fiber matrix in treatment of glaucoma comprising:

(i) performing a procedure for increasing the flow of aqueous humor from an eye, the procedure including implanting a drainage device in the eye, the drainage device being adapted to increase the flow of aqueous humor from the eye; and (ii) implanting a fiber matrix such that the fiber matrix covers at least a portion of the drainage device, between the portion of the drainage device and the conjunctiva of the eye, the fiber matrix comprising a plurality of crossing fibers forming a mesh with a plurality of void spaces;

wherein the fiber matrix, by the size and arrangement of the fibers and void spaces of the fiber matrix, permits passage of aqueous humor through the fiber matrix and inhibits formation of scar tissue through the fiber matrix.

34. A method of using a fiber matrix in treatment of glaucoma comprising:

(i) performing a procedure for increasing the flow of aqueous humor from an eye, the procedure including cutting scleral tissue to create a scleral flap, wherein the scleral flap is separated from adjacent scleral tissue at a cut opening;

(ii) lifting the scleral flap to allow access to a scleral well beneath the scleral flap;

(iii) positioning a fiber matrix such that a first part of the fiber matrix is located in the scleral well and a second part of the fiber matrix is located outside of the scleral well, wherein the fiber matrix comprises a plurality of crossing fibers forming a mesh with a plurality of void spaces; and (iv) replacing the scleral flap such that the first part of the fiber matrix is implanted under the scleral flap and the second part of the fiber matrix is implanted outside of the scleral flap, with the fiber matrix extending from inside the scleral well to outside the scleral well through the cut opening;

wherein the fiber matrix, by the size and arrangement of the fibers and void spaces of the fiber matrix, permits passage of aqueous humor through the fiber matrix and inhibits formation of scar tissue through the fiber matrix.

35. A method of using a fiber matrix in treatment of glaucoma as recited in claim 34, wherein the fiber matrix has a generally planar shape.

36. A method of using a fiber matrix in treatment of glaucoma as recited in claim 34, wherein the fibers are nonwoven.

37. A method of using a fiber matrix in treatment of glaucoma as recited in claim 34, wherein the fibers comprise a polymeric material.

38. A method of using a fiber matrix in treatment of glaucoma as recited in claim 34, wherein the fiber matrix is manufactured by electrospinning.

39. A method of using a fiber matrix in treatment of glaucoma as recited in claim 34, wherein the fibers comprise a biostable material.

40. A method of using a fiber matrix in treatment of glaucoma as recited in claim 34, wherein the fibers comprise a biodegradable material.

41. A method of using a fiber matrix in treatment of glaucoma as recited in claim 34, wherein the fibers comprise a first set of fibers formed of a biostable material and a second set of fibers formed of a biodegradable material.

42. A method of using a fiber matrix in treatment of glaucoma as recited in claim 34, further comprising using a biodegradable material to at least partially impede passage of fluid through the fiber matrix until degradation of the biodegradable material.

43. A method of using a fiber matrix in treatment of glaucoma as recited in claim 34, wherein the fiber matrix comprises suture holes for securing the fiber matrix.

44. A method of using a fiber matrix in treatment of glaucoma as recited in claim 34, further comprising using a therapeutic agent carried by the fiber matrix.

45. A method as claimed in claim 34, wherein the scleral flap comprises at least three sides, wherein the fiber matrix is implanted such that the first part of the fiber matrix is located under the scleral flap and portions making up the second part of the fiber matrix extend outside of the scleral flap at each of the three sides, and further comprising suturing the scleral flap to surrounding scleral tissue at locations between adjacent sides.

* * * * *